United States Patent
Kudo et al.

(10) Patent No.: US 12,266,517 B2
(45) Date of Patent: Apr. 1, 2025

(54) METHOD FOR EVALUATING MASS SPECTROMETRY DEVICE, METHOD FOR CALIBRATING MASS SPECTROMETRY DEVICE, ANALYSIS METHOD, MASS SPECTROMETRY DEVICE, AND MASS SPECTROMETRY REAGENT

(71) Applicant: SHIMADZU CORPORATION, Kyoto (JP)

(72) Inventors: Yukihiko Kudo, Kyoto (JP); Kenichi Obayashi, Kyoto (JP); Katsuhiro Nakagawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 797 days.

(21) Appl. No.: 17/278,905

(22) PCT Filed: Sep. 28, 2018

(86) PCT No.: PCT/JP2018/036545
§ 371 (c)(1),
(2) Date: Mar. 23, 2021

(87) PCT Pub. No.: WO2020/066009
PCT Pub. Date: Apr. 2, 2020

(65) Prior Publication Data
US 2022/0051885 A1 Feb. 17, 2022

(51) Int. Cl.
*G01N 21/64* (2006.01)
*B01F 23/00* (2022.01)
(Continued)

(52) U.S. Cl.
CPC .......... *H01J 49/0009* (2013.01); *G01N 27/62* (2013.01); *G01N 30/7206* (2013.01); *G01N 30/7233* (2013.01); *H01J 49/004* (2013.01)

(58) Field of Classification Search
CPC .. H01J 49/0009; H01J 49/004; H01J 49/0045; H01J 49/0027; G01N 27/62;
(Continued)

(56) References Cited

U.S. PATENT DOCUMENTS

| 2002/0023670 A1 | 2/2002 | Shiramizu et al. |
| 2017/0146497 A1* | 5/2017 | Akiyama ................ H01J 49/10 |
| 2021/0210322 A1* | 7/2021 | Wamsley .............. H01J 49/405 |

FOREIGN PATENT DOCUMENTS

| JP | 2000-294530 A | 10/2000 |
| JP | 2008-232844 A | 10/2008 |
| JP | 2017-096695 A | 6/2017 |

OTHER PUBLICATIONS

Jeon, So Hyeon, et al. "Development and validation of gas chromatography-triple quadrupole mass spectrometric method for quantitative determination of regulated plasticizers in medical infusion sets." Journal of Analytical Methods in Chemistry 2018 (2018). (Year: 2018).*

(Continued)

*Primary Examiner* — Jennifer Wecker
*Assistant Examiner* — Oyeleye Alexander Alabi
(74) *Attorney, Agent, or Firm* — Sughrue Mion, PLLC

(57) ABSTRACT

A method for evaluating a mass spectrometry device includes: by a mass spectrometry device, performing mass spectrometry of an ester of phthalic acid and detecting a plurality of types of ions produced by dissociation of the ester of phthalic acid; and obtaining information concerning whether the mass spectrometry device is in a state suitable for analysis, based on a ratio of intensities of the plurality of types of ions detected.

14 Claims, 4 Drawing Sheets

Diisobutyl phthalate

Dibutyl phthalate

Butylbenzyl phthalate

Di-(2-ethylhexyl) phthalate

Di-n-octhyl phthalate

Di-iso-nonyl phthalate

Diisodecyl phthalate

(51) Int. Cl.

| | |
|---|---|
| *B01F 23/41* | (2022.01) |
| *B01F 101/23* | (2022.01) |
| *B23Q 17/24* | (2006.01) |
| *C07K 14/705* | (2006.01) |
| *C12M 1/34* | (2006.01) |
| *C12Q 1/04* | (2006.01) |
| *C12Q 1/18* | (2006.01) |
| *C12Q 1/686* | (2018.01) |
| *G01N 21/3577* | (2014.01) |
| *G01N 21/359* | (2014.01) |
| *G01N 21/39* | (2006.01) |
| *G01N 21/45* | (2006.01) |
| *G01N 21/77* | (2006.01) |
| *G01N 21/78* | (2006.01) |
| *G01N 27/414* | (2006.01) |
| *G01N 27/62* | (2021.01) |
| *G01N 30/12* | (2006.01) |
| *G01N 30/68* | (2006.01) |
| *G01N 30/70* | (2006.01) |
| *G01N 30/72* | (2006.01) |
| *G01N 30/88* | (2006.01) |
| *G01N 33/00* | (2006.01) |
| *G01N 33/18* | (2006.01) |
| *G01N 33/50* | (2006.01) |
| *G01N 33/53* | (2006.01) |
| *G01N 33/543* | (2006.01) |
| *G01N 33/68* | (2006.01) |
| *G01N 33/74* | (2006.01) |
| *G01N 35/00* | (2006.01) |
| *G01N 35/10* | (2006.01) |
| *G06K 7/10* | (2006.01) |
| *G06K 7/14* | (2006.01) |
| *G06K 19/06* | (2006.01) |
| *G06K 19/07* | (2006.01) |
| *G06T 7/00* | (2017.01) |
| *G06T 7/90* | (2017.01) |
| *H01J 49/00* | (2006.01) |
| *H10K 10/46* | (2023.01) |
| *H10K 85/00* | (2023.01) |
| *H10K 85/20* | (2023.01) |

(58) Field of Classification Search
CPC ........... G01N 30/7206; G01N 30/7233; G01N 2430/00; G01N 33/50; G01N 2560/00
See application file for complete search history.

(56) References Cited

OTHER PUBLICATIONS

Kodakami. ("Development of a Novel Automated Identification and Quantification System with a Database for GC-MS", 2013) (Year: 2013).*

Shafikova, T. N., et al. "Ortho-phthalic acid esters suppress the phytopathogen capability for biofilm formation." Doklady Biological Sciences. Vol. 480. Pleiades Publishing, 2018. (Year: 2018).*

Yassin A. Jeilani et al., "Density Functional Theory and Mass Spectrometry of Phthalate Fragmentations Mechanisms: Modeling Hyperconjugated Carbocation and Radical Cation Complexes with Neutral Molecules", J. Am. Soc. Mass Spectrom, 2011, vol. 22, 12 pages.

US Environmental Protection Agency, "Method 625: Base/Neutrals and Acids, Appendix A to Part 136 Methods for Organic Chemical Analysis of Municipal and Industrial Wastewater", US Environmental Protection Agency, 1984, 42 pages.

Yuki Sakamoto et al., "Analysis of Phthalate Esters in Children's Toys using GC-MS", Shimadzu, https://www.an.shimadzu.co.jp/gcms/support/lib/pdf/c146-0274.pdf, 2011, 14 pages.

Bunseki Kagaku et al., "Reproducibility of Measurement Results by Automated Identification and Quantification System with Database for GC/MS" The Japan Society for Analytical Chemistry, 2011, vol. 60, No. 7, 2011, 9 pp. 543-556.

Kiwao Kadokami, "Development of a Novel Automated Identification and Quantification System with a Database for GC-MS", Shimadzu, https://www.an.shimadzu.co.jp/gcms/support/lib/pdf/c146-0297.pdf, 2012, 14 pages.

Kumitaka Maruyama, et al., "Screening of Phthalates in Polymer Materials by Pyrolysis GC/MS", Analytical Sciences, vol. 31, 2015, 3 pages.

Kiwao Kadokami et al., "Novel gas chromatography—mass spectrometry database for automatic identification and quantification of micropollutants", Journal of Chromatography A, 1089 (2005) 219-226.

International Search Report for PCT/JP2018/036545 dated Dec. 18, 2018.

Office Action issued Dec. 21, 2021 in Japanese Application No. 2020-547872.

Chinese Office Action dated Jan. 31, 2024 in Application No. 201880097108.3.

Office Action issued Jul. 25, 2024 in Chinese Application No. 201880097108.3.

Communication issued Dec. 10, 2024 in corresponding Chinese Patent Application No. 201880097108.3.

* cited by examiner

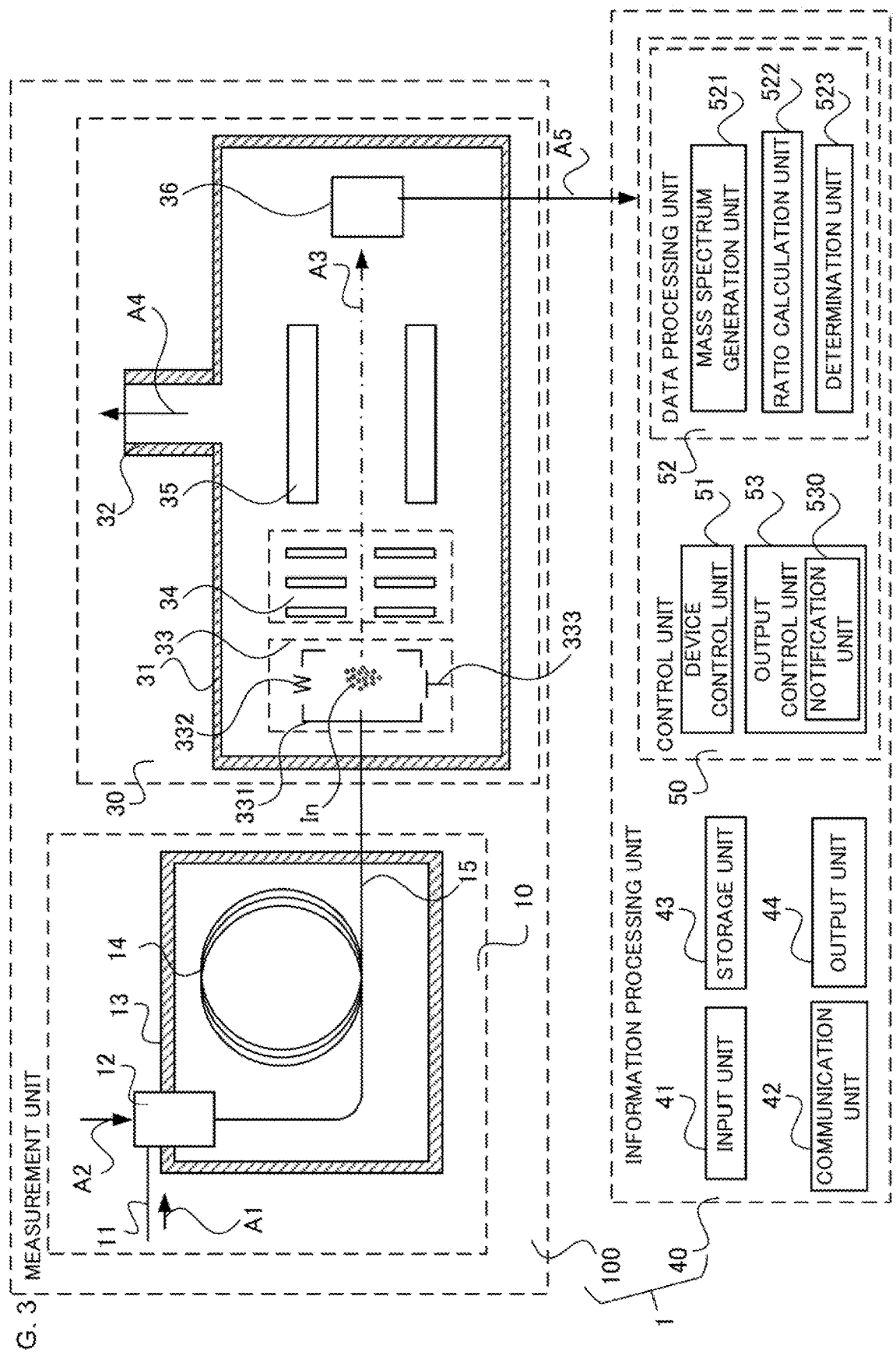

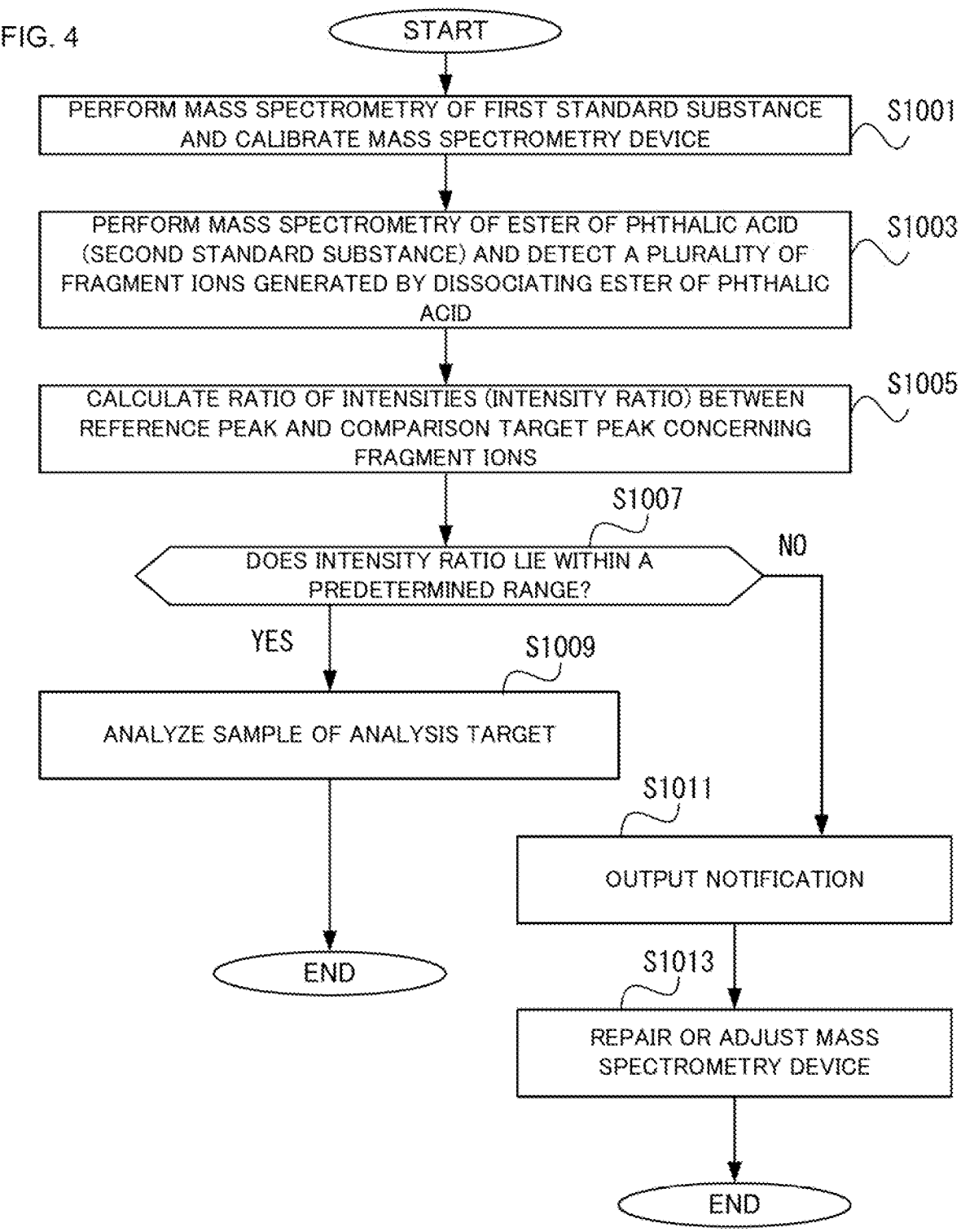

METHOD FOR EVALUATING MASS SPECTROMETRY DEVICE, METHOD FOR CALIBRATING MASS SPECTROMETRY DEVICE, ANALYSIS METHOD, MASS SPECTROMETRY DEVICE, AND MASS SPECTROMETRY REAGENT

CROSS-REFERENCE TO RELATED APPLICATIONS

This application is a National Stage of International Application No. PCT/JP2018/036545 filed Sep. 28, 2018.

TECHNICAL FIELD

The present invention relates to a method for evaluating a mass spectrometry device, a method for calibrating a mass spectrometry device, an analysis method, a mass spectrometry device, and a mass spectrometry reagent.

BACKGROUND ART

A lot of types of chemical substances are produced and used. Some chemical substances are regulated because they are, for instance, harmful to a human body and the environment. For example, phthalate esters are used as plasticizers for resins (see NPTL1). In addition to some of them being regulated in Japan, the United States, China, etc., phthalate esters will be regulated in Europe by the RoHS Directive from 2019 onwards. As the types of chemical substances that can be analysis targets are increasing as described above, attempts are being made to measure many types of components at the same time, and it has become more important to accurately measure analysis target components.

In analyses by a mass spectrometry device, different mass spectra may be obtained even if the same compound is analyzed, depending on the type and state of the device. Therefore, a first standard substance for mass calibration is measured, and mass calibration (calibration of a horizontal axis of a mass spectrum) is performed by the calibration program. Furthermore, in order to calibrate intensity variation depending on the cleavage conditions or m/z, a second standard substance is analyzed to confirm whether a relative intensity between peaks of a mass spectrum is in an appropriate range. As the second standard substance, perfluorotributylamine (PFTBA) or decafluorotriphenylphosphine (DFTPP) is known (see NPTL2).

CITATION LIST

Non-Patent Literature

NPTL 1: Jeilani Y A, Cardelino B H, Ibeanusi V M. "Density functional theory and mass spectrometry of phthalate fragmentations mechanisms: modeling hyperconjugated carbocation and radical cation complexes with neutral molecules" Journal of the American Society for Mass Spectrometry, (USA), Springer-Verlag, Aug. 11, 2011, Volume 22, 1999, doi:10.1007/s13361-011-0215-8

NPTL 2: US Environmental Protection Agency, "Method 625: Base/Neutrals and Acids", [online], 1984, US Environmental Protection Agency, [Search on Sep. 18, 2018], internet (https://www.epa.gov/sites/production/files/2015-10/documents/method_625_1984.pdf#search=%27method+625%27)

SUMMARY OF INVENTION

Technical Problem

The structures of PFTBA and DFTPP are different from the structures of chemical substances such as ester of phthalic acid. Therefore, even if it was determined that the calibration is performed correctly in the evaluation of a mass spectrometry device using PFTBA or DFTPP, there actually were some cases where the mass spectrometry device was in a state not suitable for analysis of the above chemical substances.

Solution to Problem

According to the 1st aspect of the present invention, a method for evaluating a mass spectrometry device comprises: by a mass spectrometry device, performing mass spectrometry of an ester of phthalic acid and detecting a plurality of types of ions produced by dissociation of the ester of phthalic acid; and obtaining information concerning whether the mass spectrometry device is in a state suitable for analysis, based on a ratio of intensities of the plurality of types of ions detected.

According to the 2nd aspect of the present invention, in the method for evaluating a mass spectrometry device according to the 1st aspect, it is preferred that the information is acquired based on a plurality of the ratios of intensities between detected three or more types of the ions.

According to the 3rd aspect of the present invention, in the method for evaluating a mass spectrometry device according to the 1st or 2nd aspect, it is preferred that the ester of phthalic acid is an ortho form ester of phthalic acid.

According to the 4th aspect of the present invention, in the method for evaluating a mass spectrometry device according to any one of the 1st to 3rd aspects, it is preferred that the ester of phthalic acid is selected from the group consisting of diisobutyl phthalate (DIBP), dibutyl phthalate (DBP), butylbenzyl phthalate (BBP), di-(2-ethylhexyl) phthalate (DEHP), di-n-octyl phthalate (DNOP), di-iso-nonyl phthalate (DINP), diisodecyl phthalate (DIDP), mono(2-ethylhexyl) phthalate, dimethyl phthalate (DMP), diethyl phthalate (DEP), dipropyl phthalate, bis(2-methoxyethyl) phthalate, bis(2-butoxyethyl) phthalate, n-pentyl-isopentyl phthalate, bis(2-propylheptyl) phthalate, di-n-pentyl phthalate (DPENP), diisopentyl phthalate (DPENP), di-n-hexyl phthalate (DHEXP), diisohexyl phthalate, dicyclohexyl phthalate (DCHP), dibenzyl phthalate, diheptyl phthalate, diisoheptyl phthalate, dinonyl phthalate, didecyl phthalate, diundecyl phthalate, diisoundecyl phthalate and diisotridecyl phthalate.

According to the 5th aspect of the present invention, in the method for evaluating a mass spectrometry device according to the 4th aspect, it is preferred that the ester of phthalic acid is di-(2-ethylhexyl) phthalate (DEHP).

According to the 6th aspect of the present invention, in the method for evaluating a mass spectrometry device according to any one of the 1st to 5th aspects, it is preferred that the plurality of types of ions detected include an ion corresponding to a peak having a m/z value in the range of 148 or more and 150 or less.

According to the 7th aspect of the present invention, in the method for evaluating a mass spectrometry device according to the 6th aspect, it is preferred that determining whether or not the mass spectrometry device is in a state suitable for analysis is performed, based on, among the peaks corresponding to the plurality of types of ions detected, whether or not a ratio, of an intensity of a predetermined peak to an intensity of a peak whose m/z value is in the range of 148 or more and 150 or less, is in a predetermined range.

According to the 8th aspect of the present invention, in the method for evaluating a mass spectrometry device according to the 7th aspect, it is preferred that the ester of phthalic acid is di-(2-ethylhexyl) phthalate (DEHP); the predetermined peak is at least one of a first peak whose m/z value is in the range of 278 or more and 280 or less, a second peak having whose m/z value is in the range of 166 or more and 168 or less, a third peak whose m/z value is in the range of 112 or more and 114 or less, a fourth peak whose m/z value is in the range of 70 or more and 72 or less, and a fifth peak whose m/z value is in the range of 50 or more and 58 or less; and the predetermined range for the first peak is 5% or more and 15% or less, the predetermined range for the second peak is 33% or more and 48 or less, and the predetermined range for the third peak is 8% or more and 16% or less, the predetermined range for the fourth peak is 17% or more and 30% or less, and the predetermined range for the fifth peak is 17% or more and 44% or less.

According to the 9th aspect of the present invention, in the method for evaluating a mass spectrometry device according to any one of the 1st to 8th aspects, it is preferred that the ester of phthalic acid is dissociated by electron ionization, positive ion chemical ionization, negative ion chemical ionization, or atmospheric pressure chemical ionization, or collision-induced dissociation.

According to the 10th aspect of the present invention, the method for evaluating a mass spectrometry device according to any one of the 1st to 9th aspects further comprises: outputting a notification in a case where the mass spectrometry device is not in a state suitable for analysis.

According to the 11th aspect of the present invention, a method for calibrating a mass spectrometry device comprises: performing an evaluation of a mass spectrometry device by the method for evaluating a mass spectrometry device according to any one of the 1st to 10th aspects; and performing calibration of the mass spectrometry device based on the evaluation.

According to the 12th aspect of the present invention, an analysis method comprises: performing an evaluation of a mass spectrometry device by the method for evaluating a mass spectrometry device according to any one of the 1st to 10th aspects; and performing an analysis using the mass spectrometry device.

According to the 13th aspect of the present invention, in the analysis method according to the 12th aspect, it is preferred that performing calibration of data obtained by the analysis based on the ratio of intensities of the plurality of types of ions detected.

According to the 14th aspect of the present invention, a mass spectrometry device comprises: a mass spectrometry unit that performs mass spectrometry of an ester of phthalic acid and detects a plurality of types of ions generated by dissociating the ester of phthalic acid; and an information acquisition unit that acquires information concerning whether the mass spectrometry device is in a state suitable for analysis based on the ratio of intensities of the plurality of types of ions detected.

According to the 15th aspect of the present invention, a mass spectrometry reagent for evaluating a mass spectrometry device based on a ratio of intensities of a plurality of types of ions produced by dissociation of the ester of phthalic acid obtained by mass spectrometry, comprises an ester of phthalic acid.

Advantageous Effects of Invention

According to the present invention, it is possible to accurately evaluate whether or not the mass spectrometry device is in a state suitable for analysis of chemical substances such as ester of phthalic acid.

BRIEF DESCRIPTION OF DRAWINGS

FIG. 3 is a schematic view showing a configuration of a mass spectrometry device according to one embodiment.

FIG. 4 is a flowchart showing flow of an analysis method according to the embodiment.

DESCRIPTION OF EMBODIMENTS

Figure 1:
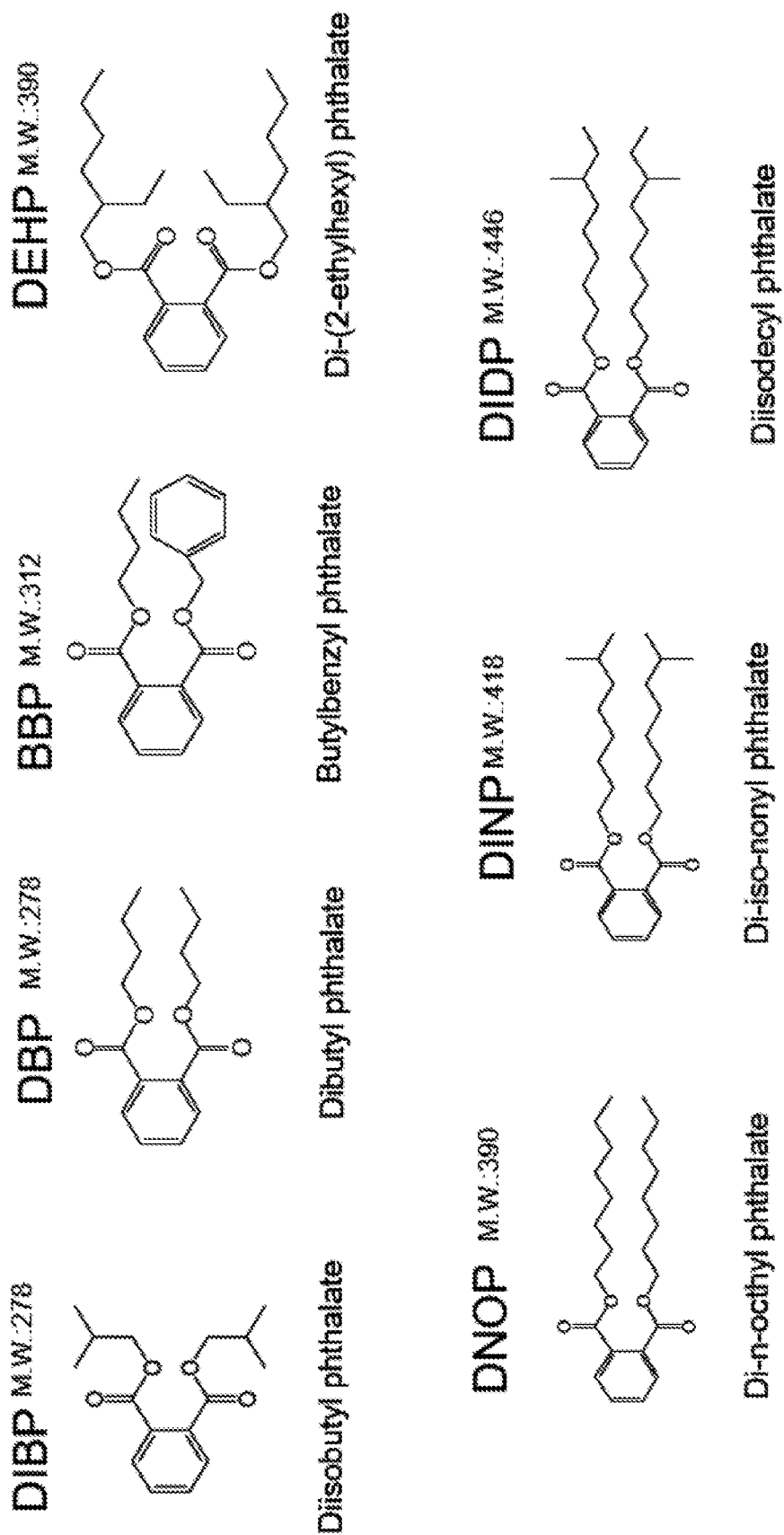
FIG. 1 is a diagram showing chemical formulas of phthalate esters.

Hereinafter, embodiments for carrying out the present invention will be described with reference to the drawings. In the following embodiments, "phthalate ester" refers to ortho form ester of phthalic acid, and "ester of phthalic acid" refers to any type of ester of ortho form, iso form, or tele form of phthalic acid.

First Embodiment

In the method for evaluating the mass spectrometry device of the present embodiment, mass calibration of the mass spectrometry device is performed using a first standard substance, and then, using a second standard substance containing an ester of phthalic acid, information concerning whether or not the mass spectrometry device is in a suitable condition for analyzing a target substance in analysis.

Standard Substance

As long as m/z at the peak to be detected corresponding to the first standard substance is known, the first standard substance is not particularly limited, and a known mass calibration reagent or the like can be used as the first standard substance. Ester of phthalic acid may also be used as the first standard substance. It is preferable that the first standard substance be the same compound as the ester of phthalic acid used for the second standard substance described later because calibration with the first standard substance and evaluation with the second standard substance can be performed at the same time. In mass calibration, a plurality of different first standard substances each having a known m/z are detected by mass spectrometry, and calibration data such as a calibration curve showing a deviation between the detected value and an actual value is generated.

The second standard substance contains ester of phthalic acid, and preferably contains phthalate ester (the ortho form). The reason for this is as follows: harmfulness of the phthalate ester has been pointed out and thus highly need to be an analysis target. If the structure of a second standard substance and the structure of an analysis target are similar, more accurate evaluation of the mass spectrometry device is possible.

It is more preferable that the second standard substance contain phthalate ester represented by the following formula (1) in which R1 and R2 are each independently an alkyl group or an aryl group having 20 or less of carbon number. Currently, many of the phthalate ester used for plasticizers or the like have 12 or less of carbon number. In a case that these are set as analysis targets, in order to make more accurate evaluation due to similarity in structure with the second standard substance, it is more preferable that the second standard substance contain phthalate ester represented by the following formula (1) in which R1 and R2 are each independently an alkyl group or an aryl group having 12 or less of carbon number.

[Chemical Formula 1]

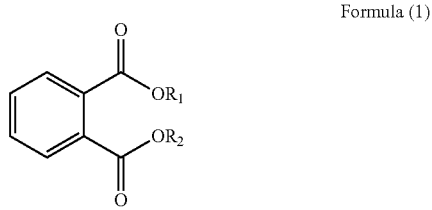

Formula (1)

From the same point of view, the second standard substance preferably contains a compound selected from diisobutyl phthalate (DIBP), dibutyl phthalate (DBP), butylbenzyl phthalate (BBP), di-(2-ethylhexyl) phthalate (DEHP), di-n-octyl phthalate (DNOP), di-iso-nonyl phthalate (DINP), diisodecyl phthalate (DIDP), mono-(2-ethylhexyl) phthalate, dimethyl phthalate (DMP), diethyl phthalate (DEP), dipropyl phthalate, bis(2-methoxyethyl) phthalate, bis(2-butoxyethyl) phthalate, n-pentyl-isopentyl phthalate, bis(2-propylheptyl) phthalate, di-n-pentyl phthalate (DPENP), diisopentyl phthalate (DPENP), di-n-hexyl phthalate (DHEXP), diisohexyl phthalate, dicyclohexyl phthalate (DCHP), dibenzyl phthalate, diheptyl phthalate, diisoheptyl phthalate, dinonyl phthalate, didecyl phthalate, diundecyl phthalate, diisoundecyl phthalate and diisotridecyl phthalate.

The second standard substance preferably contains a compound selected from diisobutyl phthalate (DIBP), dibutyl phthalate (DBP), benzylbutyl phthalate (BBP), di-(2-ethylhexyl) phthalate (DEHP), di-n-octyl phthalate (DNOP), di-iso-nonyl phthalate (DINP) and diisodecyl phthalate (DIDP). The reason for this is that these compounds are subject to regulation in the United States, Europe, etc., and thus highly need to be analysis target, and more accurate calibration can be performed because the structure of the compound of the analysis target and the second standard substance are similar. From the similar viewpoint, it is further preferable to use DEHP, which is widely used as a typical general-purpose plasticizer, as the second standard substance.

FIG. 1 is a diagram showing chemical formulas of DIBP, DBP, BBP, DEHP, DNOP, DINP, and DIDP. In FIG. 1, "M.W." indicates the molecular weight.

In the evaluation of the mass spectrometry device using the second standard substance, fragment ions obtained by dissociating the second standard substance (hereinafter, simply referred to as fragment ions) through mass spectrometry are detected, and a mass spectrum, in which peaks corresponding to the fragment ions are shown, is generated. Of the plurality of peaks corresponding to a plurality of the detected fragment ions, the ratio of the intensities (hereinafter referred to as an intensity ratio) of a predetermined peak (hereinafter referred to as a comparison target peak) with respect to a peak for reference (hereinafter referred to as a reference peak) is obtained. Based on whether or not this intensity ratio is within a predetermined range (hereinafter referred to as an allowable range), it is determined whether or not the mass spectrometry device is in a state suitable for analysis.

Figure 2:
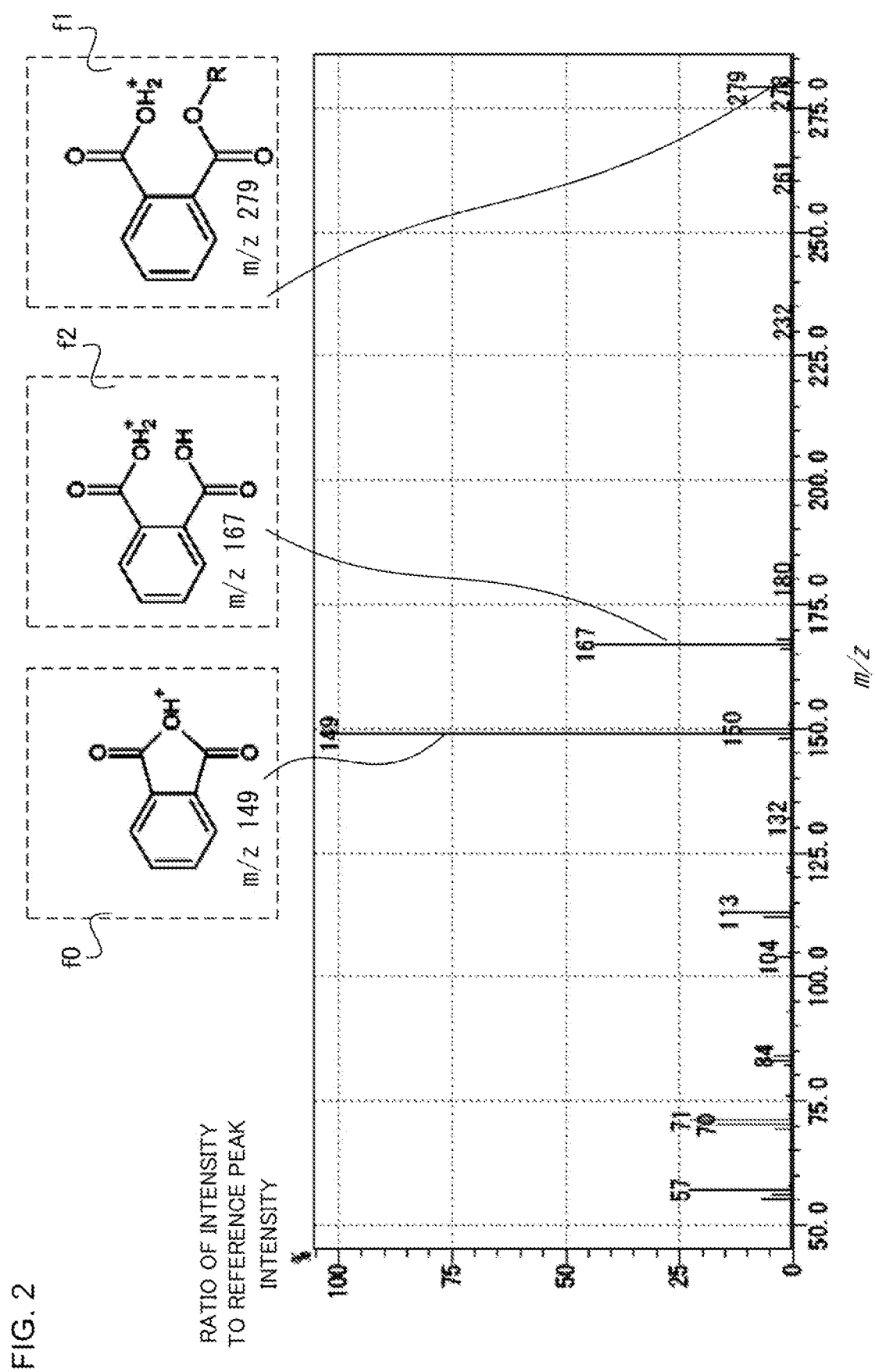
FIG. 2 is a diagram schematically showing an example of a mass spectrum obtained by dissociating di-(2-ethylhexyl) phthalate (DEHP).

FIG. 2 is a diagram schematically showing an example of a mass spectrum obtained by dissociating DEHP. In many types of phthalate esters, the peak corresponding to m/z 149 is detected as the most prominent peak in the mass spectrum showing fragment ions. Therefore, it is preferable to use the peak corresponding to this m/z 149 as the reference peak. In FIG. 2, the chemical formula of the fragment ion f0 corresponding to this reference peak is shown. By considering the variation in measurement, the reference peak can be set as a peak that lies in the range of m/z value of 148 or more and 150 or less, preferably a peak with the highest detected intensity in this range. Here, "detected intensity" is a value indicating the magnitude of detection signal corresponding to a type of fragment ions, and is quantified by the peak maximum intensity, the peak area, or the like.

As the comparison target peak, it is preferable to select at least one peak having detected intensity that is relatively high among the peaks, excluding the reference peak, in the mass spectrum showing fragment ions.

In a case that DEHP is used as the second standard substance, as the comparison target peaks, it is preferable to select at least one of; a first peak whose m/z value is in the range of 278 or more and 280 or less, a second peak whose m/z value is in the range of 166 or more and 168 or less, a third peak whose m/z value is in the range of 112 or more and 114 or less, a fourth peak whose m/z value is in the range of 70 or more and 72 or less, and a fifth peak whose m/z value is in the range of 56 or more and 58 or less. Among the peaks in each of these ranges, a peak with the highest detected intensity can be used as the comparison target peak. In FIG. 2, the chemical formulas of the fragment ions f1 and f2 corresponding to the first peak and the second peak, respectively, are shown. The first, second, third, fourth and fifth peaks are peaks corresponding to m/z values 279, 167, 113, 71 and 57, respectively.

It is preferable that the allowable range for the first peak be 5% or more and 15% or less, the allowable range for the second peak be 33% or more and 48 or less, and the allowable range for the third peak be 8% or more and 16% or less, the allowable range for the fourth peak be 17% or more and 30% or less, and the allowable range for the fifth peak be 17% or more and 44% or less.

It is to be noted that the selection, the number and the allowable range of the reference peaks and the comparison target peaks are not limited to the above example, and these can be appropriately set based on the mass spectrum showing fragment ions obtained by mass spectrometry of the second standard substance to be used.

Compound of Analysis Target

The compound to be analysis target is not particularly limited. An ester of phthalic acid may be selected as appropriate and used as the second standard substance according to m/z of the peak corresponding to the compound of the analysis target. The compound to be the analysis target is preferably ester of phthalic acid, more preferably phthalate ester (ortho form). This is because, the evaluation can be performed more accurately if the compound of the analysis target and the second standard substance have similar structures. With respect to phthalate esters, even in the case of different types of phthalate esters, the mass spectrum patterns of fragment ions of these are similar to each other, and the same reference peak (m/z 149) can be obtained. Therefore, even if the compound of the analysis target and the second standard substance are phthalate esters whose types are different from each other, evaluation can be done fairly accurately. In the method for evaluating the mass spectrometry device according to the present embodiment, information concerning whether or not the mass spectrometry device is in a state suitable for analysis of these compounds of the analysis targets is obtained.

Mass Spectrometry Device

FIG. 3 is a schematic view showing a configuration of a mass spectrometry device according to the present embodiment. A mass spectrometry device 1 is a gas chromatograph-mass spectrometer (hereinafter referred to as GC-MS), and includes a measurement unit 100 and an information processing unit 40. The measuring unit 100 includes a gas chromatograph 10 and a mass spectrometry unit 30.

It is to be noted, the mass spectrometry device according to the present embodiment is not particularly limited as long as it can ionize and dissociate the ester of phthalic acid and detect the fragment ion obtained by the dissociation, and for example, it may be a liquid chromatography-mass spectrometer (LC-MS).

The gas chromatograph 10 includes a carrier gas flow path 11, a sample of analysis target, a sample introduction unit 12 into which a sample of analysis target, the first standard substance and the second standard substance (hereinafter referred to as "sample or the like") are introduced, a column temperature control unit 13, a separation column 14 and a sample gas introduction tube 15. The mass spectrometry unit 30 includes a vacuum vessel 31, an evacuation port 32, an ionization unit 33 that ionizes a sample or the like to generate ions In, an ion adjustment unit 34, a mass separation unit 35, and a detection unit 36. The ionization unit 33 includes an ionization chamber 331, a thermoelectron generation filament 332, and a trap electrode 333.

The information processing unit 40 includes an input unit 41, a communication unit 42, a storage unit 43, an output unit 44, and a control unit 50. The control unit 50 includes a device control unit 51, a data processing unit 52, and an output control unit 53. The data processing unit 52 includes a mass spectrum generation unit 521, a ratio calculation unit 522, and a determination unit 523. The output control unit 53 includes a notification unit 530.

The measurement unit 100 separates each component of a sample or the like by separation analysis and detects the sample or the like.

The gas chromatograph 10 separates components contained in a sample or the like based on a physical or chemical property thereof. When the sample or the like is introduced into the separation column 14, the sample or the like is in the form of gas or gaseous, which is called a sample gas.

The carrier gas flow path 11 is a flow path for a carrier gas such as helium, and introduces the carrier gas into the sample introduction unit 12 (arrow A1). The sample introduction unit 12 is provided with a chamber such as a sample vaporization chamber to which the sample or the like is introduced, and temporarily receives the sample or the like injected by an injector such as a syringe or an auto sampler (not shown) and then introduces the sample gas into the separation column 14 (arrow A2). If the sample or the like is a liquid, it is vaporized and introduced into the separation column 14 as the sample gas. The method for introducing the sample or the like is not particularly limited, and a splitless injection method, a split injection method, or the like can be appropriately used.

The separation column 14 includes a column such as a capillary column. The temperature of the separation column 14 is controlled to such as several hundred ° C. or less by the column temperature control unit 13 provided with a column oven or the like. Each component of the sample gas is separated based on, for example, the partition coefficient between the mobile phase and the stationary phase of the separation column 14. Each separated component of the sample gas elutes from the separation column 14 in a different time from each other and is introduced into the ionization chamber 331 of the mass spectrometry unit 30 through the sample gas introduction tube 15.

The mass spectrometry unit 30 includes a mass spectrometer, ionizes the sample or the like introduced into the ionization unit 33, and mass-separates and detects the sample or the like. The path of the ions In generated by the ionization unit 33 is schematically shown by arrow A3.

It is to be noted that in the following, the mass spectrometry unit 30 will be described as an example of using a single quadrupole mass spectrometer which performs mass-separation by one quadrupole mass filter. However, the type of mass spectrometer constituting the mass spectrometry unit 30 is not particularly limited as long as the ions In dissociated by ionization such as electron ionization can be detected by mass spectrometry. The mass spectrometer may also be a tandem mass spectrometer or a multi-stage mass spectrometer. In the case of a configuration in which dissociation of the second standard substance or the like is not performed during ionization, the second standard substance or the like may be dissociated through collision-induced dissociation (CID) or the like using a tandem mass spectrometer or a multi-step mass spectrometer.

The vacuum vessel 31 of the mass spectrometry unit 30 is provided with the evacuation port 32. The evacuation port 32 is connected to a vacuum evacuation system (not shown in the figure) including a pump such as a turbo molecular pump capable of realizing a high vacuum of $10^{-2}$ Pa, for example, or less and an auxiliary pump. In FIG. 1, evacuation of the gas inside the vacuum vessel 31 is schematically indicated by arrows A4.

The ionization unit 33 of the mass spectrometry unit 30 includes an ion source, ionizes the sample or the like introduced into the ionization unit 33 by electron ionization. The ionization unit 33 accelerates thermoelectrons generated by the thermoelectron generation filament 332 with a voltage of such as several tens of eV applied to the trap electrode 333 and generates ions In by irradiating the sample or the like inside the ionization chamber 331 with the thermoelectrons. Since the sample or the like is dissociated at the time of ionization, the ions In contains fragment ions obtained by dissociating the sample or the like. The ions In generated in the ionization unit 33 is introduced into the ion adjustment unit 34.

It is to be noted, the method of ionization by the ionization unit 33 is not particularly limited as long as dissociation occurs, and for example, chemical ionization such as positive ion chemical ionization, negative ion chemical ionization, or an atmospheric pressure chemical ionization may be used. Further, in a case that a mass spectrometer or the like having two or more stages is used and dissociation is performed after ionization, the ionization method is not particularly limited.

The ion adjustment unit 34 of the mass spectrometry unit 30 is provided with an ion transport system such as a lens electrode, an ion guide or the like and performs adjustment by, for example, converging the ions In through an electromagnetic action. The ions In emitted from the ion adjustment unit 34 is introduced into the mass separation unit 35.

The mass separation unit 35 of the mass spectrometry unit 30 includes a quadrupole mass filter and mass-separates the introduced ions In. The mass separation unit 35 selectively passes the ions In according to m/z values by a voltage applied to the quadrupole mass filter. The ions In having mass-separated by the mass separation unit 35 is incident to the detection unit 36.

It is to be noted that the mass analyzer constituting the mass separation unit is not particularly limited, and a time-of-flight mass analyzer may be used.

The detection unit 36 of the mass spectrometry unit 30 includes an ion detector, and detects the incident ions In. The detection unit 36 performs A/D conversion of detection signal obtained by detecting the incident ions In by an A/D converter (not shown in the figure) and outputs digitized detection signal to the control unit 50 of the information processing unit 40 as measurement data (arrow A5).

The information processing unit 40 is provided with an information processing device such as a computer and serves as an interface with a user, and also performs processing such as communication, storage, and calculation related to various data.

It is to be noted that the information processing unit 40 may be configured as one device integrated with the measurement unit 100. Further, a part of the data used by the mass spectrometry device 1 may be stored in a remote server or the like, and a part of the arithmetic processing performed by the mass spectrometry device 1 may be performed by a remote server or the like.

The input unit 41 is configured to include an input device such as a mouse, a keyboard, various buttons, and/or a touch panel. The input unit 41 receives from the user information necessary for controlling the measurement unit 100 and for processing performed by the control unit 50. The communication unit 42 is configured to include a communication device capable of communicating by a wireless or wired connection via a network such as the internet, and appropriately transmits and receives such as data necessary for controlling the measurement unit 100 and for processing performed by the control unit 50.

The storage unit 43 is configured to include a non-volatile storage medium. The storage unit 43 stores measurement data, a program for the control unit 50 to execute processing, necessary data for the data processing unit 52 to execute processing, and data obtained by the processing and the like. The output unit 44 is configured to include a display device such as a liquid crystal monitor and/or a printer. The output unit 44 outputs notification saying it is determined by the method for evaluating the mass spectrometry device according to the present embodiment that the mass spectrometry device 1 is not in a state suitable for analysis, or outputs data or the like obtained through the processing of the data processing unit 52, by displaying on the display device and/or printing by the printer.

The control unit 50 includes a processor such as a CPU, controls the operation of each unit of the measurement unit 100, and processes measurement data.

The device control unit 51 of the control unit 50 controls the operation of each unit of the measurement unit 100. For example, the device control unit 51 can detect ions In by a scan mode in which m/z of the ions passed by the mass separation unit 35 is continuously changed. In this case, the device control unit 51 changes a voltage of the mass separation unit 35 so that, the ions In, having m/z in the set range (for example, 30 to 500, etc.) based on such as the input from the input unit 41, selectively pass through the mass separation unit 35. Further, in performing calibration such as mass calibration, the device control unit 51 controls the voltage value and the like of each part of the mass spectrometry device 1.

The data processing unit 52 of the control unit 50 processes and analyzes the measurement data. The data processing unit 52 analyzes the mass spectrum of the fragment ions of the second standard substance and acquires information concerning whether or not the mass spectrometry device 1 is in a state suitable for analysis. In addition to this, the data processing unit 52 can perform various analyses such as quantification of a sample of analysis target.

The mass spectrum generation unit 521 creates data corresponding to the mass spectrum (hereinafter referred to as mass spectrum data) by associating m/z values of the ions In and the intensities of the detection signal.

The ratio calculation unit 522 detects the reference peak and the comparison target peak from the mass spectrum of the fragment ions of the second standard substance and calculates the ratio of intensity detected for the comparison target peak with respect to intensity detected for the reference peak (intensity ratio). For example, the ratio calculation unit 522 refers to data, that is stored in the storage unit 43 or the like, indicating ranges (m/z 148 to 150, etc.) in which a reference peak and a comparison target peak should be detected, and determines a peak with the highest intensity detected in each range as the reference peak and the comparison target peak, respectively.

The determination unit 523 determines whether or not the mass spectrometry device is in a state suitable for analysis based on the intensity ratio calculated. The determination unit 523 refers to the value of the above-mentioned allowable range stored in the storage unit 43 or the like and determines whether or not the intensity ratio calculated is included in the allowable range (hereinafter, referred to as intensity ratio determination). In a case where a plurality of comparison target peaks exist, the determination unit 523 performs the intensity ratio determination for each comparison target peak, and if even one of them is not allowable, may determine that the mass spectrometry device 1 is not in a state suitable for analysis.

The output control unit 53 generates an output image including information or the like indicating the mass spectrum or the result of the intensity ratio determination obtained by the processing of the data processing unit 52, and controls the output unit 44 to output the output image.

The notification unit 530 of the output control unit 53 outputs, in a case where the mass spectrometry device 1 is not in a state suitable for analysis, notification of this case to the user of the mass spectrometry device 1 (hereinafter, simply referred to as a user). For example, in a case where the notification unit 530 determines that the mass spectrometry device 1 is not in a state suitable for analysis as a result of the intensity ratio determination of the determination unit 523, the notification unit 350 causes the output unit 44 to output characters such as, "there is a possibility that highly accurate analysis cannot be performed" or "FAIL" to give a warning. Further, the notification unit 530 may cause the output unit 44 to output information about the comparison target peak for which the intensity ratio is determined to be out of the allowable range. This information is, for example, m/z of the comparison target peak, thereby the user is informed of which range of m/z has a problem. In a case where the mass spectrometry device 1 is determined to be in a state suitable for analysis as a result of the intensity ratio determination, the notification unit 530 may also cause the output unit 44 to output characters such as "PASS".

Analysis Method

FIG. 4 is a flowchart showing flow of an analysis method according to the present embodiment. In step S1001, the mass spectrometry unit 30 performs mass spectrometry of the first standard substance, and the device control unit 51 calibrates the mass spectrometry device 1. Upon ending step S1001, step S1003 is started. In step S1003, the mass spectrometry unit 30 performs mass spectrometry of the ester of phthalic acid (the second standard substance) and detects a plurality of types of fragment ions having been generated by dissociating the ester of phthalic acid. Upon ending step S1003, step S1005 is started.

In step S1005, the ratio calculation unit 522 calculates the ratio of the intensities (the intensity ratio) between the reference peak and the comparison target peak concerning the fragment ions. Upon ending step S1005, step S1007 is started. In step S1007, the determination unit 523 determines whether the intensity ratio is within a predetermined range (the allowable range). In a case that the intensity ratio is within the allowable range, the determination unit 523 makes affirmative determination concerning step S1007 and step S1009 is started. In a case that the intensity ratio is not within the allowable range, the determination unit 523 makes negative determination concerning step S1007 and step S1011 is started.

In step S1009, the mass spectrometry device 1 analyzes the sample of the analysis target. The information obtained in this analysis is output from the output unit 44 or the like. Upon ending step S1009, the process ends.

In step S1011, the notification unit 530 causes the output unit 44 to output notification indicating that the mass spectrometry device 1 is not in a state suitable for analysis. Upon ending step S1011, step S1013 is started. In step S1013, the user repairs or adjusts the mass spectrometry device. Upon ending step S1013, the process ends.

It is to be noted in step S1013, the device control unit 51 may calibrate the mass spectrometry device 1 based on the evaluation such as the result or the like of the intensity ratio determination.

Mass Spectrometry Reagent

In the present embodiment, a mass spectrometry reagent for evaluating a mass spectrometry device based on the ratio of the intensities, which was obtained by mass spectrometry, with respect to a plurality of types of fragment ions produced by dissociating an ester of phthalic acid is provided. This mass spectrometry reagent contains the second standard substance described above. This makes it possible to easily prepare a standard substance for accurate evaluation concerning whether the mass spectrometry device is in a state suitable for analysis of a chemical substance such as an ester of phthalic acid.

According to the above-described embodiment, the following effects can be obtained.

(1) The method for evaluating a mass spectrometry device according to the present embodiment comprises: by the mass spectrometry device 1, performing mass spectrometry of an ester of phthalic acid and detecting a plurality of types of ions In produced by dissociation of the ester of phthalic acid; and obtaining information concerning whether the mass spectrometry device 1 is in a state suitable for analysis, based on a ratio of intensities of the plurality of types of ions In detected. This makes it possible to perform accurate evaluation concerning whether the mass spectrometry device 1 is in a state suitable for analysis of chemical substances such as ester of phthalic acid. As being able to perform such an evaluation accurately, by collating with the analysis conditions of a generalized database, the analysis can be performed using the information of the database without creating a calibration curve for each compound of analysis target. As a result, more types of compounds can be analyzed more quickly. It is to be noted that, in the present embodiment, the "ratio" is a relationship represented by A:B, A/B, etc. between A and B, and includes the "proportion" (A/B).

(2) In the method for evaluating a mass spectrometry device according to the present embodiment, the information is acquired based on a plurality of the ratios of intensities between detected three or more types of the fragment ions. Thereby, more accurate evaluation can be performed by using the information on the intensities of three or more types of fragment ions.

(3) In the method for evaluating a mass spectrometry device according to the present embodiment, the second standard substance is phthalate ester and the plurality of types of ions In detected may include an ion corresponding to a peak having m/z value in the range of 148 or more and 150 or less. In such a case, since the mass spectrometry device 1 is evaluated using the peak commonly detected concerning the fragment ions of the phthalate ester, the evaluation can be performed accurately even in a case where various phthalate esters are analyzed.

(4) In the method for evaluating a mass spectrometry device according to the present embodiment, determining whether or not the mass spectrometry device 1 is in a state suitable for analysis may be performed, based on whether or not the ratio of the intensity of a comparison target peak with respect to the intensity of a peak whose m/z value is in the range of 148 or more and 150 or less is in a predetermined range. Accordingly, since the mass spectrometry device 1 is evaluated using the peak commonly detected in the fragment ions of the phthalate ester, the evaluation can be performed further accurately even in a case where various phthalate esters are analyzed.

(5) In the method for evaluating a mass spectrometry device according to the present embodiment, the ester of phthalic acid is dissociated by electron ionization, positive ion chemical ionization, negative ion chemical ionization, or atmospheric pressure chemical ionization, or collision-induced dissociation. Accordingly, accurate evaluation can be performed by using the mass spectrum information obtained by using these ionization methods in the past.

(6) In the method for evaluating a mass spectrometry device according to the present embodiment, outputting notification in a case where the mass spectrometry device 1 is not in a state suitable for analysis. Accordingly, information about the mass spectrometry device 1 can be conveyed to the user in an easy-to-understand manner.

(7) In the method for calibrating a mass spectrometry device according to the present embodiment, an evaluation of the mass spectrometry device 1 is performed by the method for evaluating a mass spectrometry device described above and calibration of the mass spectrometry device 1 may be performed based on this evaluation. Accordingly, the mass spectrometry device 1 can be efficiently calibrated based on the accurate evaluation of the mass spectrometry device 1 using the ester of phthalic acid.

(8) The analysis method according to the present embodiment comprises: performing an evaluation of the mass spectrometry device 1 by the method for evaluating a mass spectrometry device described above; and performing an analysis using the mass spectrometry device 1. Accordingly, the accuracy of the analysis obtained by the mass spectrometry device 1 can be accurately grasped.

(9) The mass spectrometry device according to the present embodiment comprises: the mass spectrometry unit 30 that performs mass spectrometry of an ester of phthalic acid and detects a plurality of types of ions In generated by dissociating the ester of phthalic acid; and the information acquisition unit (the data processing unit 52) that acquires information concerning whether the mass spectrometry unit 30 is in a state suitable for analysis based on the ratio of intensities of the plurality of types of ions In detected. This makes it possible to perform accurate evaluation concerning whether the mass spectrometry device 1 is in a state suitable for analysis of chemical substances such as ester of phthalic acid.

The following variations are also within the scope of the present invention and can be combined with the above embodiment. In the following variations, the parts of the same structure and function as those in the above-described embodiment will be referred to by the same signs, and the description thereof will be omitted as appropriate.

Variation 1

The value obtained in the analysis of the sample of analysis target in the above-described embodiment may be corrected by using the intensity ratio calculated for the second standard substance. For example, it is assumed that the intensity ratio regarding a first peak is 15%, which is within the allowable range (5% or more and 15% or less). If changing the values around m/z 279, which corresponds to the first peak, towards two-thirds thereof, the intensity ratio can be closer to the midpoint of the allowable range, 10%. Like this, in the analysis of the sample of analysis target, more accurate data can be obtained by performing such correction.

Variation 2

Since ester of phthalic acid is also used for building materials, it is also present in indoor air and atmosphere. Therefore, indoor air or atmosphere may be collected and used as the second standard substance. Accordingly, the second standard substance can be procured at, for example, a place near the mass spectrometry device 1.

Variation 3

In the above-described embodiment, the first standard substance and the second standard substance are introduced into the gas chromatograph 10, but these may be directly introduced into the ionization unit 33 of the mass spectrometry unit 30.

The present invention is not limited to the contents of the above embodiments. Other aspects conceivable within the scope of the technical idea of the present invention are also included within the scope of the present invention.

The invention claimed is:

1. A method for evaluating a mass spectrometry device, the method comprising:

by a mass spectrometry device, performing mass spectrometry of an ester of phthalic acid and detecting a plurality of types of ions produced by dissociation of the ester of phthalic acid;

obtaining information concerning whether the mass spectrometry device is in a state suitable for analysis, based on a ratio of intensities of the plurality of types of ions detected;

determining whether or not the mass spectrometry device is in a state suitable for analysis based on whether a ratio of an intensity of a predetermined peak with respect to an intensity of a reference peak is in a predetermined range; and based on a determination that the mass spectrometry device is in a state suitable for analysis, performing analysis with the mass spectrometry device, and based on a determination that the mass spectrometry device is not in a state suitable for analysis, causing an output unit to output a notification indicating that the mass spectrometry device is not in a state suitable for analysis, wherein the mass spectrometry device includes a gas chromatograph and a mass spectrometry unit;

the gas chromatograph includes a carrier gas flow path, a sample of an analysis target, a sample introduction unit into which the sample of analysis target, the first standard substance and the second standard substance are introduced, a column temperature control unit, a separation column and a sample gas introduction tube; and the mass spectrometry unit includes a vacuum vessel, an evacuation port, an ionization unit, an ion adjustment unit, a mass separation unit, and a detection unit.

2. The method for evaluating a mass spectrometry device according to claim 1, wherein:

the information is acquired based on a plurality of the ratios of intensities between detected three or more types of the ions.

3. The method for evaluating a mass spectrometry device according to claim 1, wherein:

the ester of phthalic acid is an ortho form ester of phthalic acid.

4. The method for evaluating a mass spectrometry device according to claim 3, wherein:

the ester of phthalic acid is selected from a group consisting of diisobutyl phthalate (DIBP), dibutyl phthalate (DBP), butylbenzyl phthalate (BBP), di-(2-ethylhexyl) phthalate (DEHP), di-n-octyl phthalate (DNOP), di-iso-nonyl phthalate (DINP), diisodecyl phthalate (DIDP), mono(2-ethylhexyl) phthalate, dimethyl

REFERENCE SIGNS LIST

1 . . . Mass Spectrometry Device, 10 . . . Gas Chromatograph,
12 . . . Sample Introduction Unit, 14 . . . Separation Column,
15 . . . Sample Gas Introduction Tube, 30 . . . Mass Spectrometry Unit,
33 . . . Ionization Unit, 35 . . . Mass Separation Unit, 36 . . . Detection Unit,
40 . . . Information Processing Unit, 44 . . . Output Unit, 50 . . . Control Unit,
52 . . . Data Processing Unit, 53 . . . Output Control Unit,
100 . . . Measurement Unit, 521 . . . Mass Spectrum Generation Unit,
522 . . . Ratio Calculation Unit, 523 . . . Determination Unit,
530 . . . Notification Unit, In . . . Ion.

phthalate (DMP), diethyl phthalate (DEP), dipropyl phthalate, bis(2-methoxyethyl) phthalate, bis(2-butoxyethyl) phthalate, n-pentyl-isopentyl phthalate, bis(2-propylheptyl) phthalate, di-n-pentyl phthalate (DPENP), diisopentyl phthalate (DPENP), di-n-hexyl phthalate (DHEXP), diisohexyl phthalate, dicyclohexyl phthalate (DCHP), dibenzyl phthalate, diheptyl phthalate, diisoheptyl phthalate, dinonyl phthalate, didecyl phthalate, diundecyl phthalate, diisoundecyl phthalate and diisotridecyl phthalate.

5. The method for evaluating a mass spectrometry device according to claim 4, wherein:
the ester of phthalic acid is di-(2-ethylhexyl) phthalate (DEHP).

6. The method for evaluating a mass spectrometry device according to claim 5, wherein:
the plurality of types of ions detected include an ion corresponding to a peak having a m/z value in the range of 148 to 150.

7. The method for evaluating a mass spectrometry device according to claim 6, wherein:
determining whether or not the mass spectrometry device is in a state suitable for analysis is performed, based on, among the peaks corresponding to the plurality of types of ions detected, whether or not a ratio, of an intensity of a predetermined peak to an intensity of a peak whose m/z value is in the range of 148 to 150, is in a predetermined range.

8. The method for evaluating a mass spectrometry device according to claim 7, wherein:
the predetermined peak is at least one of a first peak whose m/z value is in the range of 278 to 280, a second peak having whose m/z value is in the range of 166 to 168, a third peak whose m/z value is in the range of 112 to 114, a fourth peak whose m/z value is in the range of 70 to 72, and a fifth peak whose m/z value is in the range of 50 to 58; and
the predetermined range for the first peak is 5% to 15%, the predetermined range for the second peak is 33% to 48%, and the predetermined range for the third peak is 8% to 16%, the predetermined range for the fourth peak is 17% to 30%, and the predetermined range for the fifth peak is 17% to 44%.

9. The method for evaluating a mass spectrometry device according to claim 1, wherein:
the ester of phthalic acid is dissociated by electron ionization, positive ion chemical ionization, negative ion chemical ionization, or atmospheric pressure chemical ionization, or collision-induced dissociation.

10. The method for evaluating a mass spectrometry device according to claim 1, further comprising:
outputting a notification in a case where the mass spectrometry device is not in a state suitable for analysis.

11. A method for calibrating a mass spectrometry device, comprising:
performing an evaluation of a mass spectrometry device by the method for evaluating a mass spectrometry device according to claim 1; and
performing calibration of the mass spectrometry device based on the evaluation.

12. A mass spectrometry device, comprising:
a mass spectrometry unit that performs mass spectrometry of an ester of phthalic acid and detects a plurality of types of ions generated by dissociating the ester of phthalic acid; and at least one processor configured to:
acquire information concerning whether the mass spectrometry device is in a state suitable for analysis based on the ratio of intensities of the plurality of types of ions detected,
determine whether or not the mass spectrometry device is in a state suitable for analysis based on whether a ratio of an intensity of a predetermined peak with respect to an intensity of a reference peak is in a predetermined range,
based on a determination that the mass spectrometry device is in a state suitable for analysis, perform analysis with the mass spectrometry device, and based on a determination that the mass spectrometry device is not in a state suitable for analysis, cause an output unit to output a notification indicating that the mass spectrometry device is not in a state suitable for analysis, wherein
the mass spectrometry device includes a gas chromatograph and a mass spectrometry unit;
the gas chromatograph includes a carrier gas flow path, a sample of an analysis target, a sample introduction unit into which the sample of analysis target, the first standard substance and the second standard substance are introduced, a column temperature control unit, a separation column and a sample gas introduction tube; and
the mass spectrometry unit includes a vacuum vessel, an evacuation port, an ionization unit, an ion adjustment unit, a mass separation unit, and a detection unit.

13. A method, comprising:
using a mass spectrometry reagent to determine whether or not a mass spectrometry device is in a state suitable for analysis based on a ratio of intensities of a plurality of types of ions produced by dissociation of an ester of phthalic acid obtained by mass spectrometry, the reagent comprising an ester of phthalic acid; and
based on the mass spectrometry device being in a state suitable for analysis, performing analysis with the mass spectrometry device, and based on the mass spectrometry device not being in a state suitable for analysis, causing an output unit to output a notification indicating that the mass spectrometry device is not in a state suitable for analysis, wherein
the mass spectrometry device includes a gas chromatograph and a mass spectrometry unit;
the gas chromatograph includes a carrier gas flow path, a sample of an analysis target, a sample introduction unit into which the sample of analysis target, the first standard substance and the second standard substance are introduced, a column temperature control unit, a separation column and a sample gas introduction tube; and
the mass spectrometry unit includes a vacuum vessel, an evacuation port, an ionization unit, an ion adjustment unit, a mass separation unit, and a detection unit.

14. A method for evaluating a mass spectrometry device, the method comprising:
by a mass spectrometry device, performing mass spectrometry of an ester of phthalic acid and detecting a plurality of types of ions produced by dissociation of the ester of phthalic acid; and
obtaining information concerning whether the mass spectrometry device is in a state suitable for analysis, based on a ratio of intensities of the plurality of types of ions detected; wherein:
the ester of phthalic acid is di-(2-ethylhexyl) phthalate (DEHP), and the plurality of types of ions detected include an ion corresponding to a peak having a m/z value in the range of 148 to 150, determining whether or not the mass spectrometry device is in a state suitable for analysis is performed, based on, among the peaks corresponding to the plurality of types of ions detected, whether or not a ratio, of an intensity of a predetermined peak to an intensity of a peak whose m/z value is in the range of 148 to 150, is in a predetermined range, the predetermined peak is at least one of a first peak whose m/z value is in the range of 278 to 280, a second peak having whose m/z value is in the range of 166 to 168, a third peak whose m/z value is in the range of 112 to 114, a fourth peak whose m/z value is in the range of 70 to 72, and a fifth peak whose m/z value is in the range of 50 to 58, and the predetermined range for the first peak is 5% to 15%, the predetermined range for the second peak is 33% to 48%, and the predetermined range for the third peak is 8% to 16%, the predetermined range for the fourth peak is 17% to 30%, and the predetermined range for the fifth peak is 17% to 44%.

* * * * *